(12) United States Patent
Sugiura et al.

(10) Patent No.: US 10,995,309 B2
(45) Date of Patent: *May 4, 2021

(54) CELL CULTURE DEVICE AND CELL CULTURE METHOD

(71) Applicant: NATIONAL INSTITUTE OF ADVANCED INDUSTRIAL SCIENCE AND TECHNOLOGY, Tokyo (JP)

(72) Inventors: Shinji Sugiura, Tsukuba (JP); Taku Satoh, Tsukuba (JP); Toshiyuki Kanamori, Tsukuba (JP); Kazumi Shin, Tsukuba (JP)

(73) Assignee: NATIONAL INSTITUTE OF ADVANCED INDUSTRIAL SCIENCE AND TECHNOLOGY

( * ) Notice: Subject to any disclaimer, the term of this patent is extended or adjusted under 35 U.S.C. 154(b) by 285 days.

This patent is subject to a terminal disclaimer.

(21) Appl. No.: 16/082,345

(22) PCT Filed: Mar. 7, 2017

(86) PCT No.: PCT/JP2017/008947
§ 371 (c)(1),
(2) Date: Sep. 5, 2018

(87) PCT Pub. No.: WO2017/154880
PCT Pub. Date: Sep. 14, 2017

(65) Prior Publication Data
US 2019/0093059 A1 Mar. 28, 2019

(30) Foreign Application Priority Data
Mar. 8, 2016 (JP) .............................. JP2016-045024

(51) Int. Cl.
C12M 1/12 (2006.01)
C12M 1/02 (2006.01)
C12M 1/00 (2006.01)

(52) U.S. Cl.
CPC ............ *C12M 23/34* (2013.01); *C12M 25/02* (2013.01); *C12M 27/00* (2013.01); *C12M 29/20* (2013.01)

(58) Field of Classification Search
CPC ...... C12M 23/34; C12M 23/38; C12M 29/20; C12M 25/02; C12M 27/00
See application file for complete search history.

(56) References Cited

U.S. PATENT DOCUMENTS

2019/0093058 A1* 3/2019 Sugiura .................. C12M 25/02
2019/0093059 A1 3/2019 Sugiura

FOREIGN PATENT DOCUMENTS

EP 3279310 A1 2/2018
EP 3 428 265 A1 1/2019
(Continued)

OTHER PUBLICATIONS

International Search Report dated Apr. 11, 2017 in corresponding PCT International Application No. PCT/JP2017/008947.
(Continued)

*Primary Examiner* — Michael L Hobbs
(74) *Attorney, Agent, or Firm* — Ostrolenk Faber LLP

(57) ABSTRACT

A cell culture device includes a storage tank having one or a plurality of cell culture units. The cell culture units includes a culture liquid main chamber having a circulation space through which a culture liquid of cells circulates, a permeable membrane having one surface to which the cells are able to adhere, said one face facing the circulation space, a first culture liquid storage chamber having an airtight structure in which the culture liquid is to be stored, a second
(Continued)

culture liquid storage chamber in which the culture liquid is to be stored, a culture liquid introduction flow path that introduces the culture liquid from the first culture liquid storage chamber into the circulation space of the culture liquid main chamber, and a culture liquid lead-out flow path that introduces the culture liquid from the circulation space into the second culture liquid storage chamber.

16 Claims, 10 Drawing Sheets

(56) References Cited

FOREIGN PATENT DOCUMENTS

| EP | 3428266 A1 | 1/2019 |
|---|---|---|
| JP | 2008-086264 A | 4/2008 |
| JP | 2009-109249 A | 5/2009 |
| JP | 2009-527225 A | 7/2009 |
| JP | 2011-257238 A | 12/2011 |
| JP | 2015-073468 A | 4/2015 |
| WO | WO 2007/098027 A2 | 8/2007 |
| WO | WO 2013/086329 A1 | 6/2013 |

OTHER PUBLICATIONS

Written Opinion dated Apr. 11, 2017 in corresponding PCT International Application No. PCT/JP2017/008947.
J.W. Scannell et al., Nat. Rev. Drug Discov., 11, 191-200 (2012).
F. Pammolli et al., Nat. Rev. Drug Discov., 10, 428-438 (2011).
P.M. van Midwoud et al., Integr. Biol., 3, 509-521 (2011).
A.M. Ghaemmaghami et al., Drug Discov. Today, 17, 173-181 (2012).
S.N. Bhatia et al., Nat. Biotechnol., 32, 760-772 (2014).
M. Baker, Nature, 471, 661-665 (2011).
J.H. Sung et al., Lab Chip, 13, 1201-1212 (2013).
H.J. Kim et al.,, Lab Chip, 12, 2165-2174 (2012).
M.B. Esch et al., Biomed. Microdevices, 14, 895-906 (2012).
K.-J. Jang et al., Integr. Biol., 5, 1119-1129 (2013).
R. Booth et al., Lab Chip, 12, 1784-1792 (2012).
S. Sugiura, et al., Anal. Chem., 82, 8278-8282 (2010).
S. Sugiura, et al., Biotechnol. Bioeng., 100, 1156-1165 (2008).
K. Hattori et al., J. Biosci. Bioeng., 118, 327-332 (2014).
Y. Imura et al., Anal. Chem., 82, 9983-9988 (2010).
A.R. Perestrelo et al., Sensors, 15, 31142-31170 (2015).
U.S. Non-Final Office Action, dated Aug. 17, 2020, issued in corresponding U.S. Appl. No. 16/082,339. Total 11 pages.
International Search Report dated Apr. 11, 2017 in corresponding PCT International Application No. PCT/JP2017/008995.
Written Opinion dated Apr. 11, 2017 in corresponding PCT International Application No. PCT/JP2017/008995.

* cited by examiner

CELL CULTURE DEVICE AND CELL CULTURE METHOD

CROSS-REFERENCE TO RELATED APPLICATIONS

The present application is a 35 U.S.C. §§ 371 national phase conversion of PCT/JP2017/008947, filed Mar. 7, 2017, which claims priority to Japanese Patent Application No. 2016-045024, filed Mar. 8, 2016, the contents of which are incorporated herein by reference. The PCT International Application was published in the Japanese language.

TECHNICAL FIELD

The present invention relates to a device of culturing cells and a method of culturing cells using the device.

BACKGROUND ART

As described in Non-Patent Documents 1 and 2, development cost for pharmaceutical products in recent years has increased exponentially, and the success rate of clinical trials has decreased year by year. In addition, the cost for developing chemical products such as cosmetics has similarly increased. As the reason for this, for example, due to the species difference between animals and humans, results of animal experiments cannot be directly extrapolated to clinical trials. In addition, in the development of chemical products such as cosmetics, in some cases, it is difficult to use experimental animals, especially in Europe. Under such circumstances, there are increasing expectations for in vitro cell assays of pharmaceutical candidate compounds and chemical products in which human-derived cultured cells are used.

On the other hand, monolayer culture used in cell assays in the conventional art is often problematic in that the environment surrounding cells is greatly different from the in vivo environment, and therefore, many functions expressed in a body are lost in cultured cells. Advances in a micro-processing technique and three-dimensional culture techniques in recent years have overcome this problem, and it is expected that throughput and reliability of cell assays will be simultaneously improved (for example, Non-Patent Documents 3 and 4). In particular, the concept of organ-on-a-chip, which handles a microfluidic device for reproducing a physiological three-dimensional culture environment in vitro as an organ, has expanded, and research considering application to development of pharmaceutical products is being globally developed (for example, Non-Patent Documents 5 and 6). Furthermore, the concept of body-on-a-chip, which aims to reproduce an individual response by connecting a plurality of organ models reconstituted in vitro with each other through micro flow paths or the like has also been proposed and has been rapidly attracting attention (for example, Non-Patent Document 7).

As described above, it is expected that the reliability of cellular assays will be improved by reconstituting an organ model formed of human-derived cultured cells in vitro and reproducing physiological functions.

Most organs constituting a living body have a membrane type structure. For example, nutrients are absorbed across the mesentery in the small intestine, and metabolites and waste products are excreted in the kidneys via renal tubular epithelial cell membranes. In addition, oxygen or nutrients are supplied to surrounding tissues through the vessel wall even in blood vessels circulating in the whole body, and waste products are excreted. Membrane type culture containers such as BOYDEN CHAMBER and TRANSWELL have been used to reconstitute functions of such membrane type organs in vitro. However, in these culture containers, a liquid cannot flow on one surface side and the other surface side of the membrane. Therefore, there are problems in that a physiological function is not exhibited, the conditions of cells in the lower portion of the membrane are deteriorated, and the culture containers cannot be applied to body-on-a-chip in which a plurality of organs are linked to each other.

In order to solve these problems, organ-on-a-chip in which a membrane is disposed in a micro flow path has been reported. For example, in vitro models for the intestines (Non-Patent Documents 8 and 9), the kidneys (Non-Patent Document 10), and encephalic blood vessels (Non-Patent Document 11) have been reported. It has been reported that barrier abilities of the organ models are improved by disposing a membrane in a micro-flow path and culturing cells while applying physiological shear stress to the cells, thereby enabling a highly accurate assay (Non-Patent Documents 10 and 11). In order to use organ-on-a-chip including such a membrane for drug discovery as an alternative to animal experiments, a system that can simultaneously evaluate many kinds of compounds is necessary. On the other hand, a syringe pump or a peristaltic pump is used for liquid transfer in the above-described prior research, and therefore, it is difficult to parallelize the culture system.

The present inventors or the like have already developed a "pressure-driven type perfusion culture micro-chamber array" capable of conveniently handling a large number of drug solutions in studies so far (Non-Patent Documents 12 and 13). Then, they have developed a circulation culture system with a convenient platform and performed a user evaluation for practical use (Non-Patent Document 14 and Patent Document 1).

PRIOR ART DOCUMENTS

Patent Documents

[Patent Document 1] Japanese Unexamined Patent Application, First Publication No. 2015-073468

Non-Patent Documents

[Non-Patent Document 1] Scannell, J. W. et al. Nat. Rev. Drug Discov., 11, 191 (2012)
[Non-Patent Document 2] Pammolli, F. et al. Nat. Rev. Drug Discov., 10, 428 (2011)
[Non-Patent Document 3] van Midwoud, P. M. et al. Integr. Biol., 3, 509 (2012)
[Non-Patent Document 4] Ghaemmaghami, A. M. et al. Drug Discov. Today, 17, 173 (2012)
[Non-Patent Document 5] Bhatia, S. N. et al. Nat. Biotechnol., 32, 760 (2014)
[Non-Patent Document 6] Baker, M. Nature, 471, 661 (2011)
[Non-Patent Document 7] Sung, J. H. et al. Lab Chip, 13, 1201 (2013)
[Non-Patent Document 8] H. J. Kim, D. Huh, G. Hamilton and D. E. Ingber, Lab Chip, 12, 2165-2174 (2012).
[Non-Patent Document 9] M. B. Esch, J. H. Sung, J. Yang, C. H. Yu, J. J. Yu, J. C. March and M. L. Shuler, Biomed. Microdevices, 14, 895-906 (2012).
[Non-Patent Document 10] K.-J. Jang, A. P. Mehr, G. A. Hamilton, L. A. McPartlin, S. Chung, K.-Y. Suh and D. E. Ingber, Integr. Biol., 5, 1119-1129 (2013).

[Non-Patent Document 11] R. Booth and H. Kim, Lab Chip, 12, 1784-1792 (2012).

[Non-Patent Document 12] S. Sugiura, et al., Anal. Chem., 82, 8278 (2010)

[Non-Patent Document 13] S. Sugiura, et al., Biotechnol. Bioeng., 100, 1156 (2008)

[Non-Patent Document 14] K. Hattori, et al., J. Biosci. Bioeng., 118, 327 (2014)

SUMMARY OF THE INVENTION

Problems to be Solved by the Invention

In a cell culture device in the conventional art, since the structure of piping or the like is complicated, there are many problems such as an increase in size of the device or a complicated operation.

An object of the present invention is to provide a cell culture device which has a simple structure and is easy to operate, and a cell culture method.

Means for Solving the Problems (1) A cell culture device including: a storage tank having one or a plurality of cell culture units, in which each of the cell culture units includes a culture liquid main chamber having a circulation space through which a culture liquid of cells circulates, a permeable membrane having one surface to which the cells are able to adhere, said one face facing the circulation space, a first culture liquid storage chamber having an airtight structure in which the culture liquid is to be stored, a second culture liquid storage chamber in which the culture liquid is to be stored, a culture liquid introduction flow path that introduces the culture liquid from the first culture liquid storage chamber into the circulation space of the culture liquid main chamber, and a culture liquid lead-out flow path that introduces the culture liquid from the circulation space into the second culture liquid storage chamber, and the storage tank has a vent hole through which gas is supplied to and discharged from the first culture liquid storage chamber.

(2) The cell culture device according to (1), in which at least two of the first culture liquid storage chambers of the plurality of the cell culture units are connected with each other so that gas is able to flow therethrough.

(3) The cell culture device according to (1) or (2), in which each of the cell culture units includes a first liquid storage chamber having an airtight structure in which a liquid is to be stored, a second liquid storage chamber in which the liquid is to be stored, and a liquid lead-out flow path that introduces the liquid from a space on the other surface side of the membrane into the second liquid storage chamber, the first liquid storage chamber being a supply source of the liquid, and the storage tank has a vent hole through which gas is supplied to and discharged from the first liquid storage chamber.

(4) The cell culture device according to (3), in which at least two of the first liquid storage chambers in the plurality of the cell culture units are connected with each other so that gas is able to flow therethrough.

(5) The cell culture device according to any one of (1) to (4), in which the first culture liquid storage chamber and the second culture liquid storage chamber each have a cell-holding portion in which seeded cells are to be held.

(6) The cell culture device according to any one of (1) to (5), further including: a backflow prevention mechanism that controls flow of the culture liquid from the culture liquid lead-out flow path to the second culture liquid storage chamber.

(7) The cell culture device according to (6), in which the backflow prevention mechanism is a check valve which allows the flow of the culture liquid in a direction from the culture liquid lead-out flow path to the second culture liquid storage chamber and prevents flow in an opposite direction thereof.

(8) The cell culture device according to any one of (1) to (5), further including: a backflow prevention mechanism that controls flow of the culture liquid from the first culture liquid storage chamber to the culture liquid introduction flow path.

(9) The cell culture device according to (8), in which the backflow prevention mechanism is a Laplace valve which allows the flow of the culture liquid from the first culture liquid storage chamber to the culture liquid introduction flow path and prevents flow of gas from the first culture liquid storage chamber to the culture liquid introduction flow path.

(10) The cell culture device according to any one of (1) to (9), in which at least one of the culture liquid introduction flow path and the culture liquid lead-out flow path has a resistance flow path part of which a flow path cross-sectional area is less than or equal to $1/10$ of that of the other part.

(11) The cell culture device according to any one of (1) to (10), in which a distance of the circulation space in a thickness direction of the membrane is 1 μm to 1,000 μm.

(12) The cell culture device according to any one of (1) to (11), in which the storage tank has a container-shaped tank main body in which the culture liquid main chamber, the first culture liquid storage chamber, and the second culture liquid storage chamber are formed, and a lid portion that airtightly closes openings of the culture liquid main chamber, the first culture liquid storage chamber, and the second culture liquid storage chamber in an openable manner.

(13) The cell culture device according to (12), further including: a lid portion-pressing portion that holds the lid portion by pressing the lid portion toward the tank main body, in which the lid portion-pressing portion has a pressing member that presses the lid portion toward the tank main body.

(14) The cell culture device according to (12) or (13), in which the tank main body includes a bottom plate having the liquid lead-out flow path, and a wall portion provided on one surface of the bottom plate, and the culture liquid main chamber, the first culture liquid storage chamber, and the second culture liquid storage chamber are spaces partitioned by the bottom plate and the wall portion.

(15) The cell culture device according to (14), further including: a wall portion-pressing portion that holds the wall portion by pressing the wall portion toward the bottom plate, in which the wall portion-pressing portion has a pressing member that presses the wall portion toward the bottom plate.

(16) The cell culture device according to any one of (1) to (15), further including: pressurizing means capable of pressurizing an inside of the first culture liquid storage chamber.

(17) A cell culture method, using a cell culture device including a storage tank having one or a plurality of cell culture units, in which each of the cell culture units includes a culture liquid main chamber having a circulation space through which a culture liquid of cells circulates, a permeable membrane having one surface to which the cells are able to adhere, where said one face faces the circulation space, a first culture liquid storage chamber having an airtight structure in which the culture liquid is to be stored, a second culture liquid storage chamber in which the culture liquid is to be stored, a culture liquid introduction flow path that introduces the culture liquid from the first culture liquid storage chamber into the circulation space of the culture liquid main chamber, and a culture liquid lead-out flow path that introduces the culture liquid from the circulation space into the second culture liquid storage chamber, the storage tank having a vent hole through which gas is supplied to and discharged from the first culture liquid storage chamber, the method including: supplying gas to the first culture liquid storage chamber through the vent hole to pressurize the first culture liquid storage chamber; and introducing the culture liquid in the first culture liquid storage chamber into the culture liquid main chamber through the culture liquid introduction flow path with a pressure increase in the first culture liquid storage chamber, and introducing the culture liquid in the culture liquid main chamber into the second culture liquid storage chamber through the culture liquid lead-out flow path.

Effects of Invention

According to an aspect of the present invention, it is possible to introduce the culture liquid from the first culture liquid storage chamber into the culture liquid main chamber through the culture liquid introduction flow path by pressurizing the first culture liquid storage chamber and culture cells on the membrane in the culture liquid main chamber while exposing the cells to fluid shear stress, and it is possible to introduce the culture liquid in the culture liquid main chamber into the second culture liquid storage chamber through the culture liquid lead-out flow path. For this reason, it is possible to simplify the structure of the flow path of liquid transfer. Accordingly, it is possible to miniaturize the device by simplifying the structure of the device and to facilitate the operation.

According to the cell culture device having a plurality of cell culture units, it is possible to perform a plurality of tests in parallel through a simple operation. For this reason, it is possible to efficiently evaluate a large number of specimens (drugs and the like).

EMBODIMENTS FOR CARRYING OUT THE INVENTION

First Embodiment

[Cell Culture Device] A cell culture device 10 of a first embodiment will be described with reference to the drawings.

Figure 1:
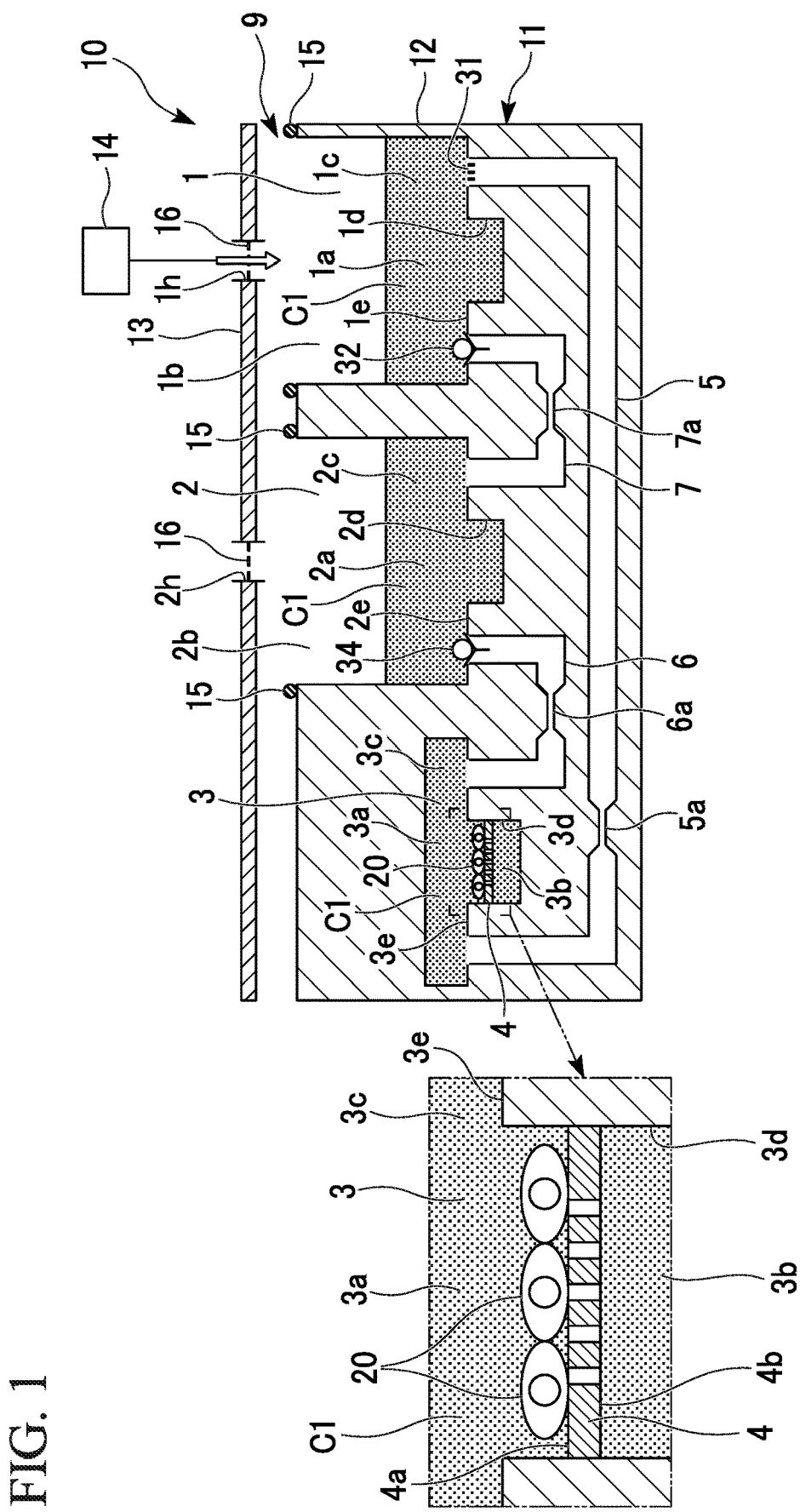
FIG. 1 is a cross-sectional view schematically showing a cell culture device of a first embodiment.
Figure 2:
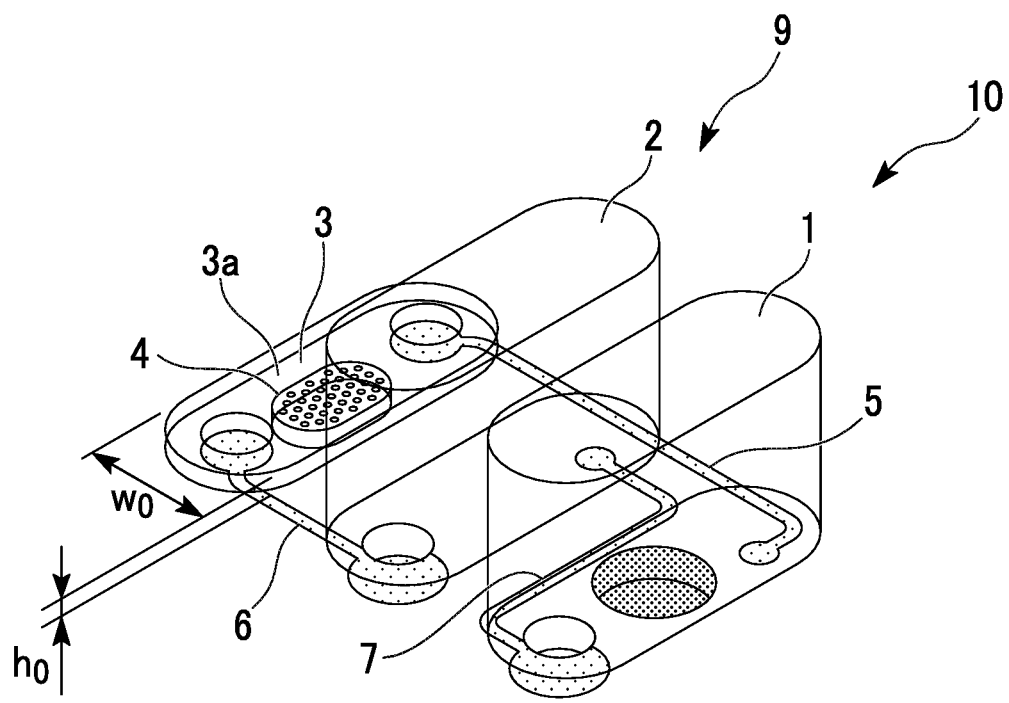
FIG. 2 is a perspective view schematically showing the cell culture device of FIG. 1.

FIG. 1 is a cross-sectional view schematically showing the cell culture device 10. FIG. 2 is a perspective view schematically showing the cell culture device 10.

As shown in FIGS. 1 and 2, the cell culture device 10 includes a storage tank 11 and a pressurizing pump 14. The storage tank 11 includes one cell culture unit 9. The storage tank 11 includes a container-shaped tank main body 12 and a lid portion 13.

The cell culture unit 9 has a culture liquid main chamber 3, a first culture liquid storage chamber 1, a second culture liquid storage chamber 2, a membrane 4, a culture liquid introduction flow path 5, a culture liquid lead-out flow path 6, and a communication flow path 7.

The culture liquid main chamber 3 has a main chamber 3c and a recess portion 3d formed in a bottom surface 3e of the main chamber 3c.

The internal space of the main chamber 3c is a circulation space 3a in which a culture liquid C1 circulates. A space on an inner surface 4a side of the membrane 4 in the internal space of the recess portion 3d is a part of the circulation space 3a. A space on an outer surface 4b side of the membrane 4 in the internal space of the recess portion 3d is an outer surface side space 3b. In FIG. 1, the outer surface side space 3b is positioned below the circulation space 3a. In the storage tank 11, it is possible to form a sampling hole (not shown in the drawings) communicating with the outer surface side space 3b. Accordingly, it is possible to collect a liquid in the outer surface side space 3b through the sampling hole. The culture liquid main chamber 3 is a hollow portion formed in the storage tank 11.

(Design Regarding Shear Stress)

By setting the height of the circulation space 3a (the distance in the thickness direction of the membrane 4) as follows, it is possible to increase the flow rate of the culture liquid C1 flowing through the circulation space 3a and to apply sufficient shear stress to the cells 20 on the membrane 4.

As shown in FIG. 2, the shear stress (τ) to be added can be estimated using Equation (1) (refer to Non-Patent Document 15: F. M. White, Viscous Fluid Flow, McGraw-Hill Companies, Inc, Boston, 2006) based on the width ($w_0$) and the height ($h_0$) of the circulation space 3a, the flow rate (Q) of the culture liquid C1, and the viscosity ($\mu$) of the culture liquid C1.

$$\tau = 6\mu \frac{Q_c}{w_0 h_0^2} \quad (1)$$

Appropriate shear stress for improving a cell function varies depending on the cells. However, the shear stress is known to be, for example, 1 to 10 dyn/cm$^2$ in a case of vascular endothelial cells (refer to Non-Patent Document 16: K. Hattori, Y. Munehira, H. Kobayashi, T. Satoh, S. Sugiura and T. Kanamori, "Microfluidic perfusion culture chip providing different strengths of shear stress for analysis of vascular endothelial function", J. Biosci. Bioeng., 118, 327-332 (2014)), and 0.2 dyn/cm$^2$ in a case of renal epithelial cells (refer to Non-Patent Document 10).

On the other hand, the amount of culture liquid per assay when being used for in vitro cell assays of pharmaceutical candidate compounds or chemical products is 10 µl to 10 ml in consideration of cost and handling. Accordingly, in order to realize appropriate shear stress, it is preferable that the height of the circulation space 3a be within a range of 1 µm to 1,000 µm from Equation (1).

The height $h_0$ of the circulation space 3a is a distance (distance in the thickness direction of the membrane 4) between the inner surface 4a (upper surface) of the membrane 4 and an inner top surface of the circulation space 3a.

Substances having a predetermined size or less are permeable through the membrane 4 in a thickness direction. The movement of substances permeating through the membrane 4 occurs, for example, by diffusion. In some cases, the substance movement may be promoted by an action of the cells 20 attached to the membrane 4. The membrane 4 may be, for example, a porous membrane. The average pore diameter of the membrane 4 is, for example, 0.1 µm to 10 µm. The material of the membrane 4 may be any one of polycarbonate, polyester, and silicone resin. The membrane 4 may be, for example, a semipermeable membrane. The cells 20 are not permeable through the membrane 4. An inner surface 4a of the membrane 4 is preferably coated with a cell adhesive material. The cell adhesive material is preferably one or more of collagen, gelatin, fibronectin, laminin, vitronectin, matrigel, and polylysine.

The membrane 4 is installed in the recess portion 3d so as to separate the circulation space 3a and the outer surface side space 3b from each other. The membrane 4 is located at a position higher than that of the bottom surface of the recess portion 3d and can be installed so as to close the recess portion 3d in parallel to the bottom surface 3e of the main chamber 3c. The inner surface 4a (one surface) of the membrane 4 faces the circulation space 3a, and the outer surface 4b (the other surface) faces the outer surface side space 3b.

The first culture liquid storage chamber 1 and the second culture liquid storage chamber 2 are spaces formed by recess portions formed on the upper surface of the tank main body 12 of the storage tank 11 and are capable of storing the culture liquid C1.

The first culture liquid storage chamber 1 has a main chamber 1c and a cell-holding recess portion 1d (cell-holding portion) formed on a bottom surface 1e of the main chamber 1c. The internal space of the first culture liquid storage chamber 1 is a culture liquid storage space 1a.

The second culture liquid storage chamber 2 has a main chamber 2c and a cell-holding recess portion 2d (cell-holding portion) formed on a bottom surface 2e of the main chamber 2c. The internal space of the second culture liquid storage chamber 2 is a culture liquid storage space 2a.

One end of the culture liquid introduction flow path 5 is connected to the bottom portion of the main chamber 1c of the first culture liquid storage chamber 1, and the other end is connected to the bottom portion of the main chamber 3c of the culture liquid main chamber 3. The culture liquid introduction flow path 5 is capable of introducing the culture liquid C1 from the first culture liquid storage chamber 1 into the circulation space 3a of the culture liquid main chamber 3.

One end of the culture liquid lead-out flow path 6 is connected to the bottom portion of the main chamber 3c of the culture liquid main chamber 3, and the other end is connected to the bottom portion of the main chamber 2c of the second culture liquid storage chamber 2. The culture liquid lead-out flow path 6 is capable of introducing the culture liquid C1 from the circulation space 3a of the culture liquid main chamber 3 into the second culture liquid storage chamber 2.

One end of the communication flow path 7 is connected to the bottom portion of the main chamber 2c of the second culture liquid storage chamber 2, and the other end is connected to the bottom portion of the main chamber 1c of the first culture liquid storage chamber 1. The communication flow path 7 is capable of introducing the culture liquid C1 from the second culture liquid storage chamber 2 into the first culture liquid storage chamber 1.

The lid portion 13 is capable of airtightly closing the opening of the tank main body 12 in an openable manner. Specifically, the lid portion 13 is capable of airtightly closing upper openings 1b and 2b of the first culture liquid storage chamber 1 and the second culture liquid storage chamber 2. An example of a structure in which the lid portion 13 airtightly closes the upper openings 1b and 2b includes a structure in which the lid portion 13 abuts on the upper surface of the tank main body 12 with a packing 15 interposed therebetween, and the packing 15 is provided so as to surround each of the upper openings 1b and 2b. In FIG. 1, the lid portion 13 is shown separately from the tank main body 12.

The lid portion 13 has vent holes 1h and 2h at positions corresponding to the first culture liquid storage chamber 1 and the second culture liquid storage chamber 2, respectively. It is possible to supply gas (for example, air) to the first culture liquid storage chamber 1 and the second culture liquid storage chamber 2 and to discharge gas (for example, air) from the first culture liquid storage chamber 1 and the second culture liquid storage chamber 2 through the vent holes 1h and 2h, respectively. It is preferable that an air filter 16 be provided in each of the vent holes 1h and 2h. It is possible to prevent foreign substances from being mixed in the first culture liquid storage chamber 1 and the second culture liquid storage chamber 2, using the air filter 16.

A Laplace valve 31 which allows flow of a liquid from the first culture liquid storage chamber 1 to the culture liquid introduction flow path 5 and prevents inflow of gas from the first culture liquid storage chamber 1 to the culture liquid introduction flow path 5 is provided at one end of the culture liquid introduction flow path 5 in the first culture liquid storage chamber 1.

A check valve 32 which allows flow of a liquid in a direction from the communication flow path 7 to the first culture liquid storage chamber 1 and prevents flow in an opposite direction thereof is provided at the other end of the communication flow path 7 in the first culture liquid storage chamber 1.

A check valve 34 which allows flow of a liquid in a direction from the culture liquid lead-out flow path 6 to the second culture liquid storage chamber 2 and prevents flow in an opposite direction thereof is provided at the other end of the culture liquid lead-out flow path 6 in the second culture liquid storage chamber 2.

(Check Valve)

An example of the check valves 32 and 34 includes a check valve having a structure including, for example, a valve seat with a valve hole and a valve body. In this check valve, when a liquid flows in a forward direction, the valve hole is opened by separating the valve body from the valve seat. Therefore, the liquid flows in the forward direction while passing through the valve hole. When the liquid flows in an opposite direction, the valve body abuts on the valve seat and the valve hole is closed. Therefore, the flow of the liquid in the opposite direction is prevented.

The check valves 32 and 34 are examples of a backflow prevention mechanism for controlling flow of a liquid.

(Laplace Valve)

Figure 10A:
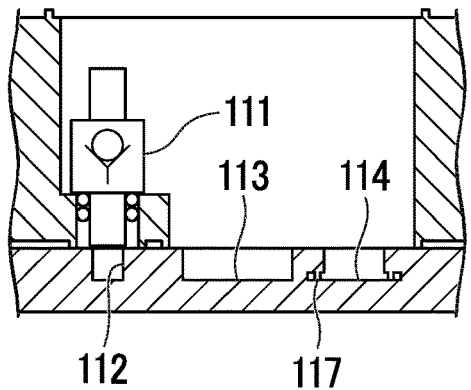
FIG. 10A is an explanatory view of a Laplace valve. Specifically, it is a partially enlarged view of a liquid storage chamber provided with a Laplace valve.
Figure 10B:
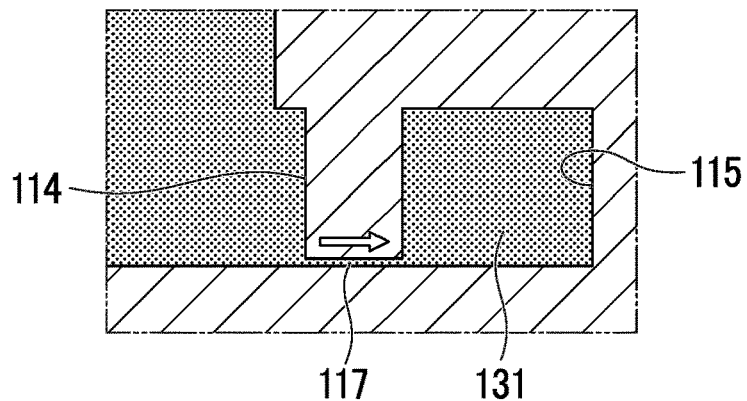
FIG. 10B is an explanatory view of the Laplace valve. Specifically, it is a schematic diagram in a case where a medium flows into a communication flow path from a downstream port through the Laplace valve.
Figure 10C:
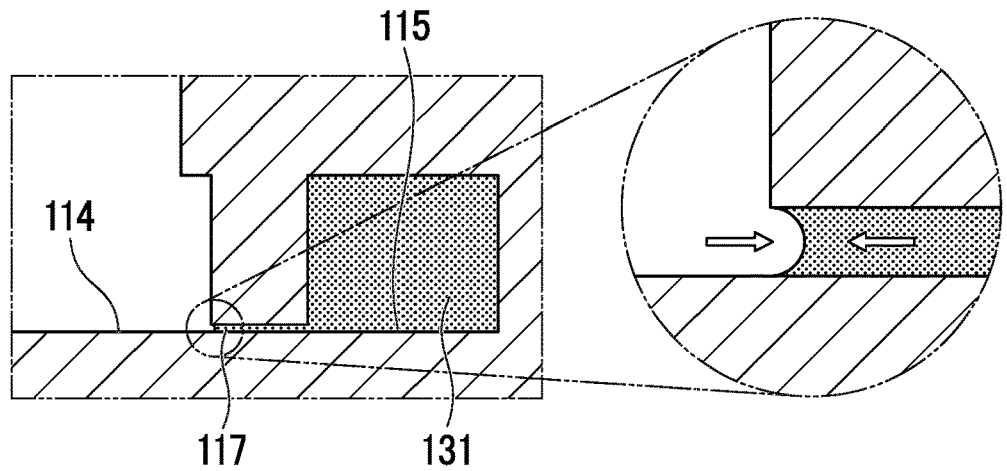
FIG. 10C is an explanatory view of the Laplace valve. Specifically, it shows a schematic diagram in a case where the Laplace valve is functioning when air has flowed into the downstream port.

The structure and function of the Laplace valve 31 will be described using FIGS. 10A to 10C. FIG. 10A shows a partially enlarged view of a liquid storage chamber provided with a Laplace valve 117. FIG. 10B shows a schematic diagram in a case where a medium 131 flows into a communication flow path 115 from a downstream port 114 through the Laplace valve 117. FIG. 10C shows a schematic diagram in a case where the Laplace valve 117 is functioning when air has flowed into the downstream port 114. As shown in FIG. 10C, a pressure difference due to interfacial tension, that is, Laplace pressure, is generated between the medium 131 and air in the micro-flow path. In a case where the surface of the flow path is wet with a liquid medium, air cannot flow into the micro-flow path filled with a liquid under the air pressure condition of less than the Laplace pressure. Under such a condition, the micro-flow path can be treated as a passive air inflow prevention mechanism.

The design of the Laplace valve will be described below.

The pressure (Laplace pressure, critical pressure) ($\Delta P_{Lap}$) at which air flows into the Laplace valve can be calculated by the interfacial tension ($\gamma$), and the width ($w_L$) and the depth ($h_L$) of the micro-flow path constituting the Laplace valve, using Equation (2).

$$\Delta P_{Lap} = 2\gamma(1/w_L + 1/h_L) \tag{2}$$

It is considered that the practical pressure range for driving the cell culture device is determined by the pressure range adjustable with a commercially available pressure control device and the pressure resistance of cells.

If the pressure resistance of cells is an upper limit (30 kPa=225 mmHg) of the blood pressure in a living body, a practical pressure range for driving the cell culture device according to the embodiment is approximately 1 kPa to 30 kPa. In a case where the interfacial tension of a culture liquid is approximately 60 mN/m and the cross section of the micro-flow path constituting the Laplace valve is square, that is, in a case where $w_L=h_L$, the size of the micro-flow path into which air flows at 30 kPa is estimated as approximately $w_L=h_L=8$ μm and the size of the micro-flow path into which air flows at 1 kPa is estimated as approximately $w_L=h_L=240$ μm, using Equation (2).

By setting the sizes of the micro-flow path constituting the Laplace valve to be smaller than the above-described sizes ($w_L=h_L=8$ μm at 30 kPa and $w_L=h_L=240$ μm at 1 kPa), it is possible to prevent air from flowing into the Laplace valve when the device is operated at an assumed pressure.

That is, if a micro-flow path constituting the Laplace valve is formed so that the Laplace pressure $\Delta P_{Lap}$, which is a critical pressure for the Laplace valve to function, is larger than the pressure range used in the cell culture device according to the embodiment, it is possible to prevent air from flowing into the Laplace valve.

Even in a case where the ratio of $w_L$ to $h_L$ is not 1:1, it is possible to design the size of the flow path based on Equation (2).

In the cell culture device 10, by respectively designing the width and the depth of the culture liquid introduction flow path 5, for example, to be 200 μm and 25 μm and estimating the Laplace pressure as 5.4 kPa, it is possible to make a liquid flow through the culture liquid introduction flow path 5 so that the pressure becomes lower than or equal to the value.

The Laplace valve 31 is an example of a backflow prevention mechanism for controlling flow of a liquid.

(Resistance Flow Path)

The flow rate (Q) and the pressure loss ($\Delta P$) of a liquid flowing through the micro-flow path having a rectangular cross section have the following relationship (refer to F. M. White, Viscous Fluid Flow, McGraw-Hill Companies, Inc, Boston, 2006).

$$\Delta P = R \times Q \tag{3}$$

$$R = \frac{12\mu l}{wh^3}\left\{1 - \frac{h}{w}\left[\frac{192}{\pi^5}\sum_{i=1,3,5}^{\infty}\frac{1}{i^5}\tanh\left(\frac{i\pi w}{2h}\right)\right]\right\}^{-1} \tag{4}$$

In Equations (3) and (4), $\Delta P$ represents a pressure difference between an inlet and an outlet of the micro-flow path, R represents a flow path resistance, μ represents a viscosity of a fluid, l represents a length of the micro-flow path, w represents a width of the micro-flow path, and h represents a depth of the micro-flow path. Equations (3) and (4) are established with a condition of w>h.

For example, in the cell culture device 10, the culture liquid introduction flow path 5, the culture liquid lead-out flow path 6, and the communication flow path 7 may include resistance flow path parts 5a, 6a, and 7a of which the flow path cross-sectional areas are less than or equal to ¹/₁₀ in order to control the flow rate.

A case where the lengths of the resistance flow path parts are equal to those of parts of other sections in the flow paths 5, 6, and 7 can be considered. In a case where the cross-sectional area of a resistance flow path is ¹/₁₀ of the cross-sectional area of the other part, the width w and the depth h become ¹/₁₀^0.5 and the flow path resistance R of the resistance flow path of Equation (4) becomes 100 times the flow path resistance R of the part other than the resistance flow path.

Regarding the pressure loss, the pressure loss in the resistance flow path becomes 100 times the pressure loss of the part other than the resistance flow path from Equation (3). When estimating the flow rate through the entire flow path, an estimation error in a case where the flow rate is estimated in consideration of only the resistance of the resistance flow path and the pressure applied to the entire flow path becomes ¹/₁₀₀, which is an acceptable error.

That is, in a case where a resistance flow path part having a flow path cross-sectional area of less than or equal to ¹/₁₀ is provided in a part of the flow path in order to control the flow rate, there is an advantage in that the design of a flow path network becomes easy by designing the flow path in consideration of only the pressure loss in the resistance flow path.

The resistance flow path part may be formed only in one of the culture liquid introduction flow path 5 and the culture liquid lead-out flow path 6.

The pressurizing pump 14 is, for example, a compressor.

[Cell Culture Method]

Next, an example of a method of culturing cells using the cell culture device 10 will be described.

Cells to be cultured in this embodiment are not particularly limited, and it is possible to use, for example, cells derived from animals including humans, cells derived from plants, and cells derived from microorganisms depending on the purpose.

(1) Step 1

As shown in FIGS. 1 and 2, the cells 20 are seeded on the inner surface 4a of the membrane 4 and are made to adhere thereto. The culture liquid C1 may be introduced into the circulation space 3a of the culture liquid main chamber 3.

Renal tubule cells, cerebrovascular endothelial cells, and the like can be used as the cells 20 to be seeded on the membrane 4. A kidney model is obtained using the renal tubule cells. A blood-brain barrier model is obtained using the cerebrovascular endothelial cells.

The culture liquid C1 is introduced into the first culture liquid storage chamber 1. Cells may be seeded in the recess portion 1d of the first culture liquid storage chamber 1. The culture liquid C1 may also be introduced into the second culture liquid storage chamber 2. Cells may be seeded in the recess portion 2d of the second culture liquid storage chamber 2. Then, the lid portion 13 is closed so as to be pressed against the packing 15, and at least the upper opening 1b of the first culture liquid storage chamber 1 is airtightly closed.

(2) Step 2

The pressurizing pump 14 is operated to pressurize the inside of the first culture liquid storage chamber 1 by supplying gas (for example, air) to the first culture liquid storage chamber 1 through the vent hole 1h. At this time, it is preferable that the second culture liquid storage chamber 2 be open to the atmosphere through the vent hole 2h.

Due to the pressure increase in the first culture liquid storage chamber 1, the culture liquid C1 in the first culture liquid storage chamber 1 is introduced into the circulation space 3a of the culture liquid main chamber 3 through the culture liquid introduction flow path 5. The culture liquid C1 in the circulation space 3a is introduced into the second culture liquid storage chamber 2 through the culture liquid lead-out flow path 6.

Since the culture liquid C1 flows from the first culture liquid storage chamber 1 to the second culture liquid storage chamber 2 via the circulation space 3a of the culture liquid main chamber 3, it is possible to culture the cells 20 in an environment where shear stress is applied to the cells.

(3) Step 3

When gas (for example, air) is supplied to the second culture liquid storage chamber 2 through the vent hole 2h using the pressurizing pump 14 to pressurize the inside of each chamber, the culture liquid C1 in the second culture liquid storage chamber 2 is introduced into the first culture liquid storage chamber 1 through the communication flow path 7 due to the pressure increase in the second culture liquid storage chamber 2. At this time, it is preferable that the first culture liquid storage chamber 1 be open to the atmosphere.

By repeating the steps 2 and 3, it is possible to circulate the culture liquid C1 among the first culture liquid storage chamber 1, the culture liquid main chamber 3 (circulation space 3a), and the second culture liquid storage chamber 2.

The influence of a substance as a specimen on the cells 20 can be evaluated by adding the substance into the system (for example, the circulation space 3a in the culture liquid main chamber 3). Examples of the substance as a specimen include chemical substances, such as pharmaceutical candidate compounds, food additives, cosmetic raw materials, paints, and agricultural chemicals, which are used in various chemical products. The specimen is not limited thereto.

In the cell culture device 10, the structure of the flow paths for liquid transfer can be simplified. Therefore, it is possible to miniaturize the device by simplifying the structure of the device and to facilitate the operation such as setting of the device. For example, in the devices shown in Non-Patent Documents 8, 10, and 11, structures are employed in which a syringe pump and a cartridge-type peristaltic pump are used for liquid transfer. Therefore, the piping connection for liquid transfer is more complicated compared to that of the present embodiment, the device increases in size, and an operation of the test is more complicated as well.

Second Embodiment

[Cell Culture Device]

A cell culture device 10A according to a second embodiment will be described with reference to the drawings. Hereinafter, the same configurations as those described above are given the same reference numerals, and the description thereof will not be repeated.

Figure 3:
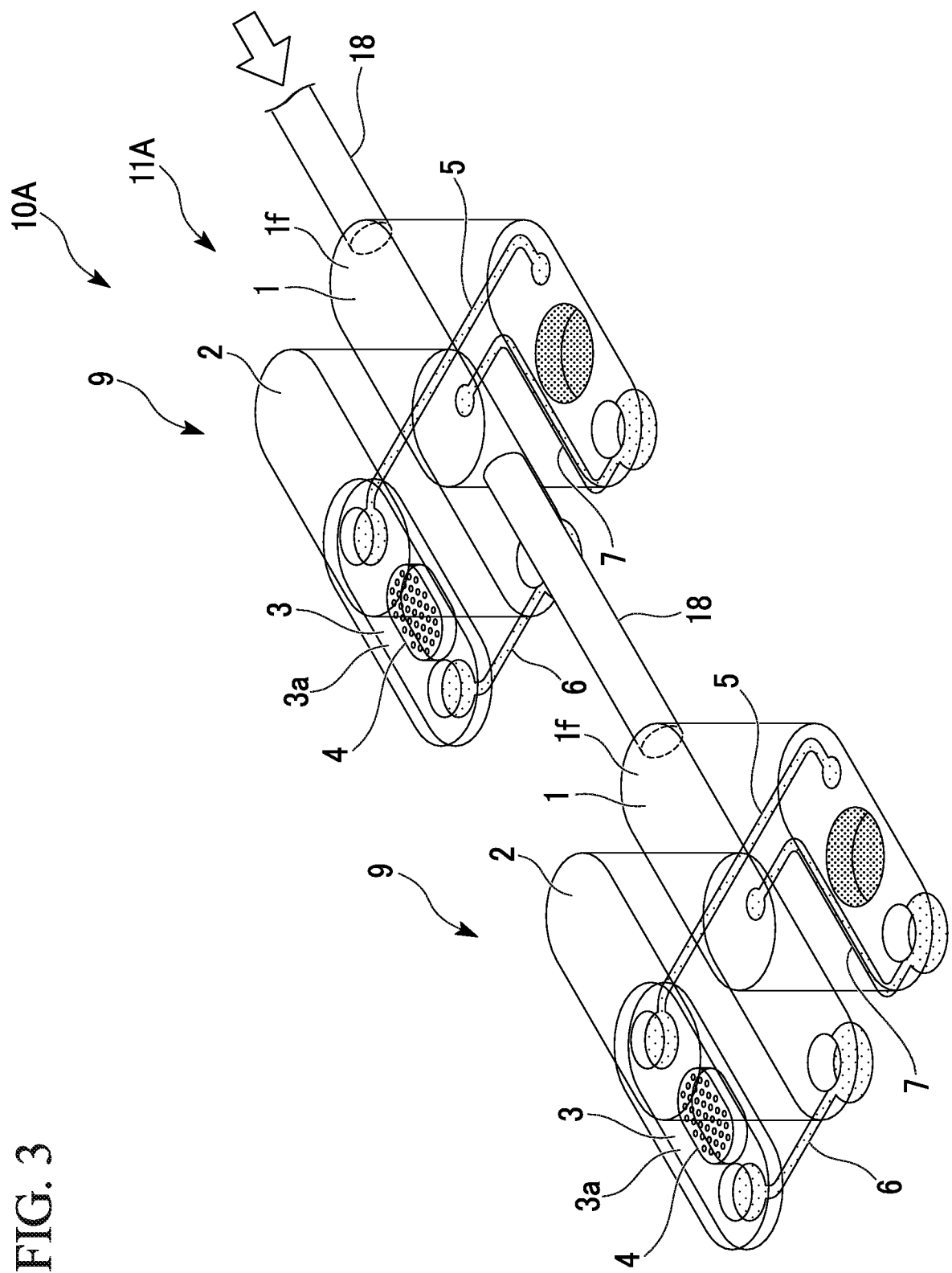
FIG. 3 is a perspective view schematically showing a cell culture device of a second embodiment.

As shown in FIG. 3, a storage tank 11A in the cell culture device 10A has a plurality of cell culture units 9. The number of cell culture units 9 may be any number of two or more.

Among the plurality of cell culture units 9, first culture liquid storage chambers 1 and 1 of two adjacent cell culture units 9 and 9 are connected with each other through a gas flow path 18 (connection flow path).

One end and the other end of the gas flow path 18 are connected to upper gas phase spaces 1f and 1f in the first culture liquid storage chambers 1 and 1, and therefore, the gas flow path 18 is connected to the first culture liquid storage chambers 1 and 1 so that gas is able to flow therethrough.

In a case where the number of cell culture units 9 is three or more, first culture liquid storage chambers 1 of at least two cell culture units 9 may be connected with each other through a gas flow path 18.

In the cell culture device 10A, when some first culture liquid storage chambers 1 out of the plurality of first culture liquid storage chambers 1 are pressurized, all the first culture liquid storage chambers 1 connected to each other through the gas flow path 18 are collectively pressurized. Therefore, it is possible to transfer a culture liquid C1 from the first culture liquid storage chamber 1 to second culture liquid storage chambers 2 via circulation spaces 3a of the culture liquid main chambers 3. For this reason, in the cell culture device 10A, it is possible to perform a plurality of tests in parallel through a simple operation.

In addition, a liquid can be transferred by a small number of pressurizing pumps 14 (refer to FIG. 1), and therefore, the structure of the device can be simplified. For this reason, it is possible to miniaturize the device by simplifying the structure of the device and to facilitate the operation such as setting of the device.

In the devices shown in Non-Patent Documents 8, 10, and 11 described above, structures are employed in which a syringe pump and a cartridge-type peristaltic pump are used for liquid transfer, and one pump and one organ-on-a-chip are used in order to evaluate one specimen.

In order to evaluate a plurality of specimens with this structure, it is necessary to add as many pumps and peristaltic pump cartridges as the number of specimens to be examined. Therefore, the number of piping connections for liquid transfer increases.

The cell culture device 10A shown in FIG. 3 is superior to the devices shown in Non-Patent Documents 8, 10, 11, and the like in that it is possible to efficiently evaluate a large number of specimens (drugs and the like) through a simple operation.

Third Embodiment

[Cell Culture Device]

A cell culture device 10B of a third embodiment will be described with reference to the drawings.

Figure 4:
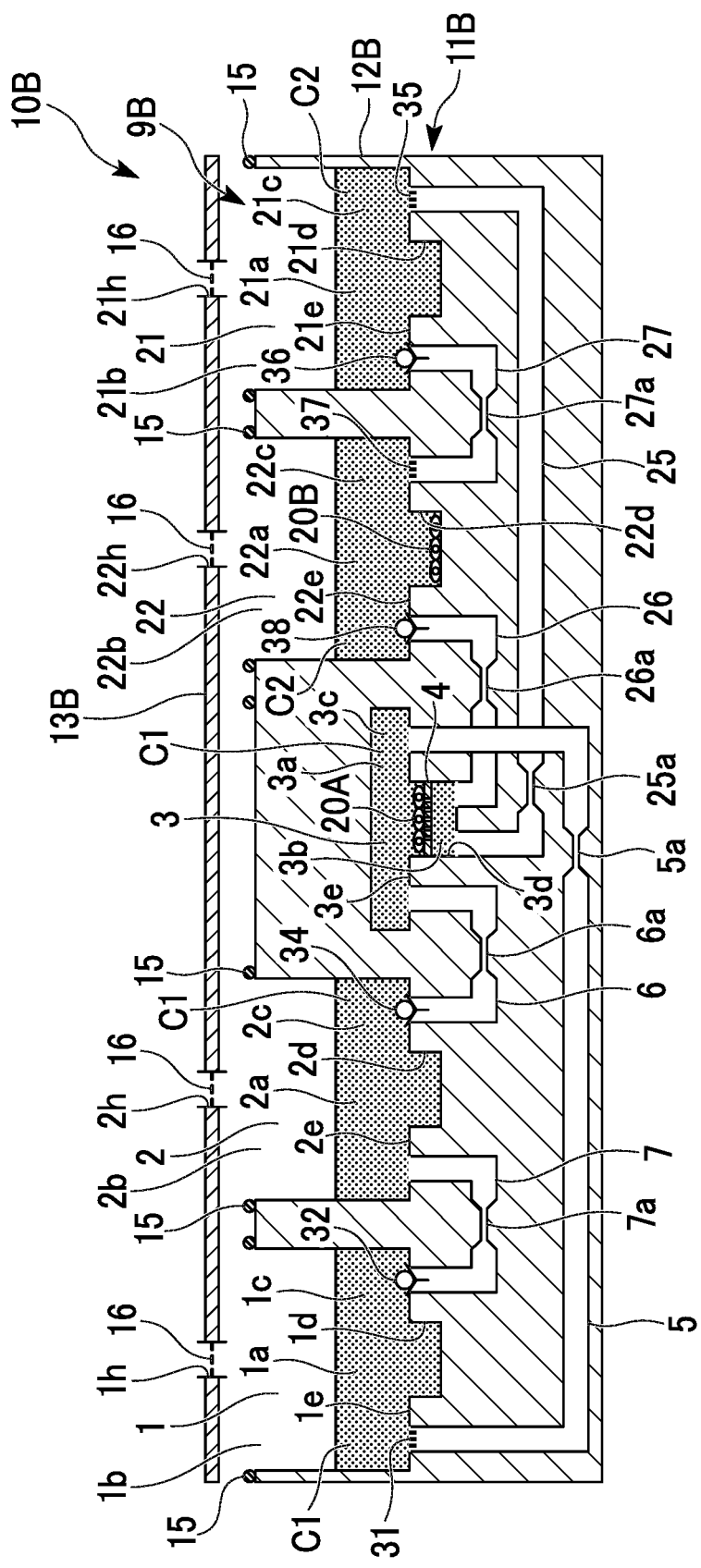
FIG. 4 is a cross-sectional view schematically showing a cell culture device of a third embodiment.

FIG. 4 is a cross-sectional view schematically showing the cell culture device 10B.

As shown in FIG. 4, the cell culture device 10B includes a storage tank 11B and a pressurizing pump (not shown in the drawings). The storage tank 11B includes one cell culture unit 9B. The storage tank 11B includes a tank main body 12B and a lid portion 13B.

The cell culture unit 9B has a culture liquid main chamber 3, a first culture liquid storage chamber 1, a second culture liquid storage chamber 2, a membrane 4, a culture liquid introduction flow path 5, a culture liquid lead-out flow path 6, a communication flow path 7, a first liquid storage chamber 21, a second liquid storage chamber 22, a liquid introduction flow path 25, a liquid lead-out flow path 26, and a communication flow path 27.

The first liquid storage chamber 21 and the second liquid storage chamber 22 are spaces formed by recess portions formed on the upper surface of the tank main body 12B of the storage tank 11B and are capable of storing a culture liquid C2.

The first liquid storage chamber 21 has a main chamber 21c and a cell-holding recess portion 21d (cell-holding portion) formed on a bottom surface 21e of the main chamber 21c. The internal space of the first liquid storage chamber 21 is a culture liquid storage space 21a.

The second liquid storage chamber 22 has a main chamber 22c and a cell-holding recess portion 22d (cell-holding portion) formed on a bottom surface 22e of the main chamber 22c. The internal space of the second liquid storage chamber 22 is a culture liquid storage space 22a.

In the first liquid storage chamber 21 and the second liquid storage chamber 22, cells different from the cells 20 in the culture liquid main chamber 3 can also be cultured. For example, vascular endothelial cells are cultured in the culture liquid main chamber 3, hepatocytes are cultured in the first liquid storage chamber 21, nerve cells are cultured in the second liquid storage chamber 22, and a specimen substance is added to the first culture liquid storage chamber 1, whereby it is possible to evaluate the influence of the specimen substance which has been cultured and has permeated through the blood vessel wall under a predetermined physiological condition (for example, shear stress load condition) on the liver or the nerves.

One end of the liquid introduction flow path 25 is connected to the bottom portion of the main chamber 21c of the first liquid storage chamber 21, and the other end is connected to the bottom portion of the recess portion 3d of the culture liquid main chamber 3. The liquid introduction flow path 25 is capable of introducing the culture liquid C2 from the first liquid storage chamber 21 into an outer surface side space 3b of the culture liquid main chamber 3.

One end of the liquid lead-out flow path 26 is connected to the bottom portion of the recess portion 3d of the culture liquid main chamber 3, and the other end is connected to the bottom portion of the second liquid storage chamber 22. The liquid lead-out flow path 26 is capable of introducing the culture liquid C2 from the outer surface side space 3b of the culture liquid main chamber 3 into the second liquid storage chamber 22.

One end of the communication flow path 27 is connected to the bottom portion of the main chamber 22c of the second liquid storage chamber 22, and the other end is connected to the bottom portion of the main chamber 21c of the first liquid storage chamber 21. The communication flow path 27 is capable of introducing the culture liquid C2 from the second liquid storage chamber 22 into the first liquid storage chamber 21.

The lid portion 13B is capable of airtightly closing the opening of the tank main body 12B in an openable manner. For example, the lid portion 13B is capable of airtightly closing upper openings 1b and 2b of the first culture liquid storage chamber 1 and the second culture liquid storage chamber 2 and upper openings 21b and 22b of the first liquid storage chamber 21 and the second liquid storage chamber 22.

An example of a structure in which the lid portion 13B airtightly closes the upper openings 1b, 2b, 21b, and 22b includes a structure in which the lid portion 13 abuts on the upper surface of the tank main body 12B with a packing 15 interposed therebetween, and the packing 15 is provided so as to surround each of the upper openings 1b, 2b, 21b, and 22b.

The lid portion 13B has vent holes 1h, 2h, 21h, and 22h at positions corresponding to the first culture liquid storage chamber 1, the second culture liquid storage chamber 2, the first liquid storage chamber 21, and the second liquid storage chamber 22, respectively. It is possible to supply gas (for example, air) to the storage chambers 1, 2, 21, and 22 and to discharge gas (for example, air) from the storage chambers 1, 2, 21, and 22 through the vent holes 1h, 2h, 21h, and 22h, respectively. It is preferable that an air filter 16 be provided in each of the vent holes 1h, 2h, 21h, and 22h.

A Laplace valve 35 which allows flow of a liquid from the first liquid storage chamber 21 to the liquid introduction flow path 25 and prevents inflow of gas from the first liquid storage chamber 21 to the liquid introduction flow path 25 is provided at one end of the liquid introduction flow path 25 in the first liquid storage chamber 21.

A check valve 36 which allows flow of a liquid in a direction from the communication flow path 27 to the first liquid storage chamber 21 and prevents flow in an opposite direction thereof is provided at the other end of the communication flow path 27 in the first liquid storage chamber 21.

A Laplace valve 37 which allows flow of a liquid from the second liquid storage chamber 22 to the communication flow path 27 and prevents inflow of gas from the second liquid storage chamber 22 to the communication flow path 27 is provided at one end of the communication flow path 27 in the second liquid storage chamber 22.

A check valve 38 which allows flow of a liquid in a direction from the liquid lead-out flow path 26 to the second liquid storage chamber 22 and prevents flow in an opposite direction thereof is provided at the other end of the liquid lead-out flow path 26 in the second liquid storage chamber 22.

Resistance flow path parts 25*a*, 26*a*, and 27*a* are respectively formed in the liquid introduction flow path 25, the liquid lead-out flow path 26, and the communication flow path 27.

[Cell Culture Method]

Next, an example of a cell culture method using the cell culture device 10B will be described.

(1) Step 1

The cells 20A are seeded on the inner surface 4*a* of the membrane 4 of the culture liquid main chamber 3 to adhere thereto. The cells 20B are seeded in the recess portion 22*d* of the second liquid storage chamber 22.

(2) Step 2

A culture liquid C1 is introduced into the second culture liquid storage chamber 2 and a culture liquid C2 is introduced into the second liquid storage chamber 22. The lid portion 13B is closed.

(3) Step 3

Gas (for example, air) is supplied to the second culture liquid storage chamber 2 and the second liquid storage chamber 22 through the vent holes 2*h* and 22*h* respectively to pressurize the inside of each of the chambers. At this time, it is preferable that the first culture liquid storage chamber 1 and the first liquid storage chamber 21 be open to the atmosphere.

Due to the pressure increase in the second culture liquid storage chamber 2, the culture liquid C1 in the second culture liquid storage chamber 2 is introduced into the first culture liquid storage chamber 1 through the communication flow path 7. Due to the pressure increase in the second liquid storage chamber 22, the culture liquid C2 in the second liquid storage chamber 22 is introduced into the first liquid storage chamber 21 through the communication flow path 27.

(4) Step 4

Gas (for example, air) is supplied to the first culture liquid storage chamber 1 and the first liquid storage chamber 21 through the vent holes 1*h* and 21*h* respectively to pressurize the inside of each of the chambers. At this time, it is preferable that the second culture liquid storage chamber 2 and the second liquid storage chamber 22 be open to the atmosphere.

Due to the pressure increase in the first culture liquid storage chamber 1, the culture liquid C1 in the first culture liquid storage chamber 1 flows in the second culture liquid storage chamber 2 via the circulation space 3*a* of the culture liquid main chamber 3 through the culture liquid introduction flow path 5. Due to the pressure increase in the first liquid storage chamber 21, the culture liquid C2 in the first liquid storage chamber 21 flows in the second liquid storage chamber 22 via the outer surface side space 3*b* of the culture liquid main chamber 3 through the liquid introduction flow path 25.

By repeating the steps 3 and 4, it is possible to circulate the culture liquid C1 among the first culture liquid storage chamber 1, the culture liquid main chamber 3 (circulation space 3*a*), and the second culture liquid storage chamber 2. In addition, it is possible to circulate the culture liquid C2 among the first liquid storage chamber 21, the culture liquid main chamber 3 (outer surface side space 3*b*), and the culture liquid lead-out flow path 22. Since it is possible to circulate the culture liquids C1 and C2, it is possible to culture the cells 20A and 20B in an environment where shear stress is applied.

In the cell culture device 10B, the structure of the flow paths for liquid transfer can be simplified. Therefore, it is possible to miniaturize the device by simplifying the structure of the device and to facilitate the operation such as setting of the device.

It is possible to use the cell culture device 10B as a model for evaluating drug transportation and expression of drug efficacy for the brain using cerebrovascular endothelial cells as the cells 20A and cranial nerve cells as the cells 20B.

Fourth Embodiment

[Cell Culture Device]

A cell culture device 10C of a fourth embodiment will be described with reference to the drawings.

Figure 5:
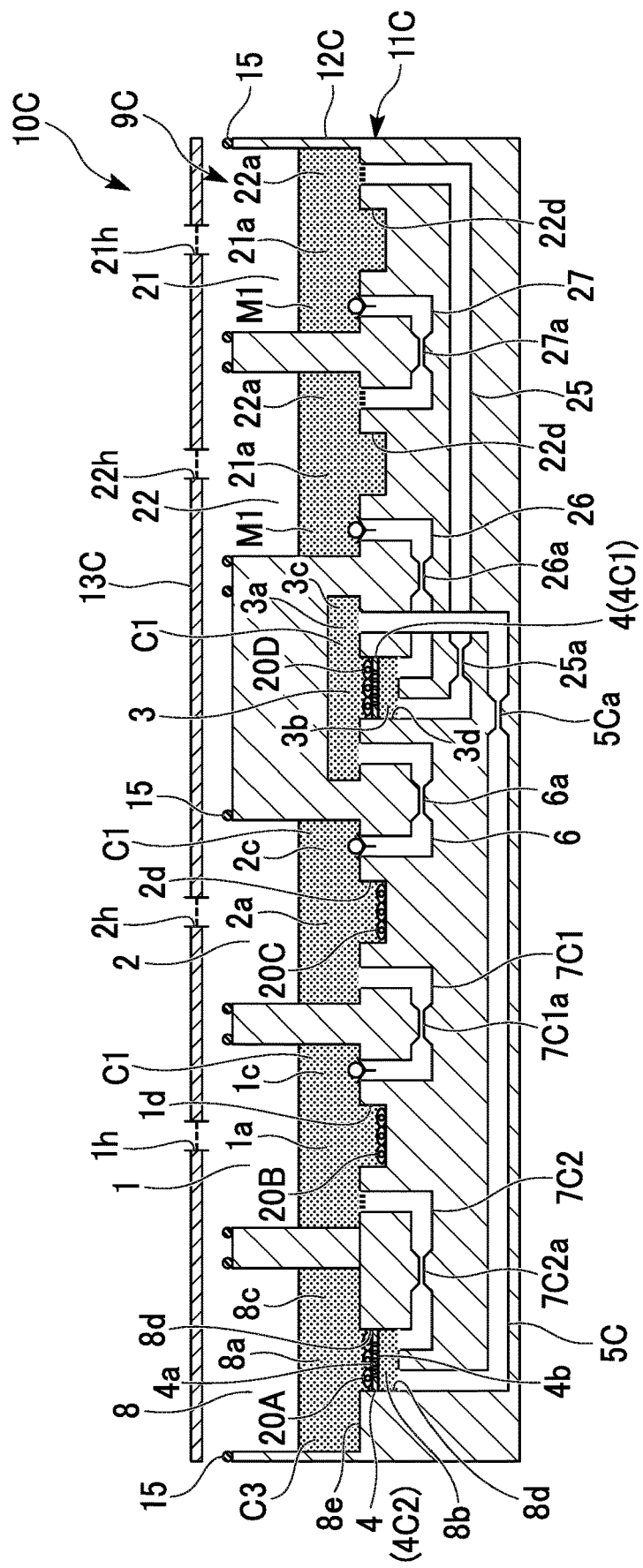
FIG. 5 is a cross-sectional view schematically showing a cell culture device of a fourth embodiment.

FIG. 5 is a cross-sectional view schematically showing the cell culture device 10C.

As shown in FIG. 5, the cell culture device 10C includes a storage tank 11C and a pressurizing pump (not shown in the drawings). The storage tank 11C includes one cell culture unit 9C. The storage tank 11C includes a tank main body 12C and a lid portion 13C.

The cell culture unit 9C has a culture liquid main chamber 3, a first culture liquid storage chamber 1, a second culture liquid storage chamber 2, a third culture liquid storage chamber 8, a membrane 4 (4C1) in the culture liquid main chamber 3, a membrane 4(4C2) in the third culture liquid storage chamber 8, a culture liquid introduction flow path 5C, a culture liquid lead-out flow path 6, a first communication flow path 7C1, a second communication flow path 7C2, a first liquid storage chamber 21, a second liquid storage chamber 22, a liquid introduction flow path 25, a liquid lead-out flow path 26, and a communication flow path 27.

The third culture liquid storage chamber 8 has a main chamber 8*c* and a recess portion 8*d* formed in a bottom surface 8*e* of the main chamber 8*c*. The internal space of the main chamber 8*c* is a storage space 8*a* in which a culture liquid C3 is to be stored. A space on an inner surface 4*a* side of the membrane 4 (4C2) provided in the recess portion 8*d* in the internal space of the recess portion 8*d* is a part of the storage space 8*a*. A space on an outer surface 4*b* side of the membrane 4 (4C2) in the internal space of the recess portion 8*d* is an outer surface side space 8*b*.

The membrane 4 (4C2) is installed so as to separate the storage space 8*a* and the outer surface side space 8*b* from each other. The inner surface 4*a* (one surface) of the membrane 4 (4C2) faces the storage space 8*a*, and the outer surface 4*b* (the other surface) faces the outer surface side space 8*b*.

One end of the culture liquid introduction flow path 5C is connected to the bottom portion of the recess portion 8*d* of the third culture liquid storage chamber 8, and the other end is connected to the bottom portion of the main chamber 3*c* of the culture liquid main chamber 3. The culture liquid introduction flow path 5C is capable of introducing the culture liquid C1 from the outer surface side space 8*b* of the third culture liquid storage chamber 8 into the circulation space 3*a* of the culture liquid main chamber 3.

One end of the first communication flow path 7C1 is connected to the bottom portion of the main chamber 2*c* of the second culture liquid storage chamber 2, and the other end is connected to the bottom portion of the main chamber 1*c* of the first culture liquid storage chamber 1. The first communication flow path 7C1 is capable of introducing the culture liquid C1 from the second culture liquid storage chamber 2 into the first culture liquid storage chamber 1.

One end of the second communication flow path 7C2 is connected to the bottom portion of the main chamber 1*c* of the first culture liquid storage chamber 1, and the other end is connected to the bottom portion of the recess portion 8d of the third culture liquid storage chamber 8. The second communication flow path 7C2 is capable of introducing the culture liquid C1 from the second culture liquid storage chamber 2 into the outer surface side space 8b of the third culture liquid storage chamber 8.

Resistance flow path parts 5Ca, 7C1a, and 7C2a are respectively formed in the culture liquid introduction flow path 5C, the first communication flow path 7C1, and the second communication flow path 7C2.

Next, an example of a cell culture method using the cell culture device 10C will be described.

(1) Step 1

Cells 20A are seeded on the inner surface 4a of the membrane 4 (4C2) in the third culture liquid storage chamber 8 and are made to adhere thereto. Cells 20B are seeded in a recess portion 1d of the first culture liquid storage chamber 1. Cells 20C are seeded in a recess portion 2d of the second culture liquid storage chamber 2. Cells 20D are seeded on an inner surface 4a of the membrane 4 (4C1) in the culture liquid main chamber 3 and are made to adhere thereto.

(2) Step 2

The culture liquid C1 is introduced into the second culture liquid storage chamber 2 and a liquid medium M1 (liquid) is introduced into the second liquid storage chamber 22, and then the lid portion 13C is closed.

(3) Step 3

Gas is supplied to the second culture liquid storage chamber 2 and the second liquid storage chamber 22 to pressurize the inside of each of the chambers.

The culture liquid C1 sequentially flows in the second culture liquid storage chamber 2, the first communication flow path 7C1, and the first culture liquid storage chamber 1.

The liquid medium M1 sequentially flows in the second liquid storage chamber 22, the communication flow path 27, and the first liquid storage chamber 21.

(4) Step 4

Gas is supplied to the first culture liquid storage chamber 1 and the first liquid storage chamber 21 to pressurize the inside of each of the chambers.

The culture liquid C1 sequentially flows in the first culture liquid storage chamber 1, the outer surface side space 8b of the third culture liquid storage chamber 8, the circulation space 3a of the culture liquid main chamber 3, and the second culture liquid storage chamber 2.

The liquid medium M1 sequentially flows in the first liquid storage chamber 21, the outer surface side space 3b of the culture liquid main chamber 3, and the second liquid storage chamber 22.

By repeating the steps 3 and 4, it is possible to circulate the culture liquid C1 among the second culture liquid storage chamber 2, the first culture liquid storage chamber 1, the third culture liquid storage chamber 8 (outer surface side space 8b), and the culture liquid main chamber 3 (circulation space 3a). In addition, it is possible to circulate the culture liquid among the second liquid storage chamber 22, the first liquid storage chamber 21, and the culture liquid main chamber 3 (outer surface side space 3b). For this reason, it is possible to cultivate the cells 20A to 20D under an environment to which shear stress is applied.

In the cell culture device 10C, the structure of the flow paths for liquid transfer can be simplified. Therefore, it is possible to miniaturize the device by simplifying the structure of the device and to facilitate the operation such as setting of the device.

It is possible to use the cell culture device 10C as a drug kinetics evaluation model and a systemic expression evaluation model to determine an anticancer effect of a drug which has been absorbed in the intestines, metabolized in the liver, and excreted in the kidneys, using intestinal epithelial cells (small intestine model) as the cells 20A, liver cells (liver model) as the cells 20B, the cancer cells (cancer model) as the cells 20C, and renal tubule cells (renal model) as the cells 20D.

A specific example of the cell culture device 10B according to the third embodiment will be described with reference to the drawings.

Figure 6:
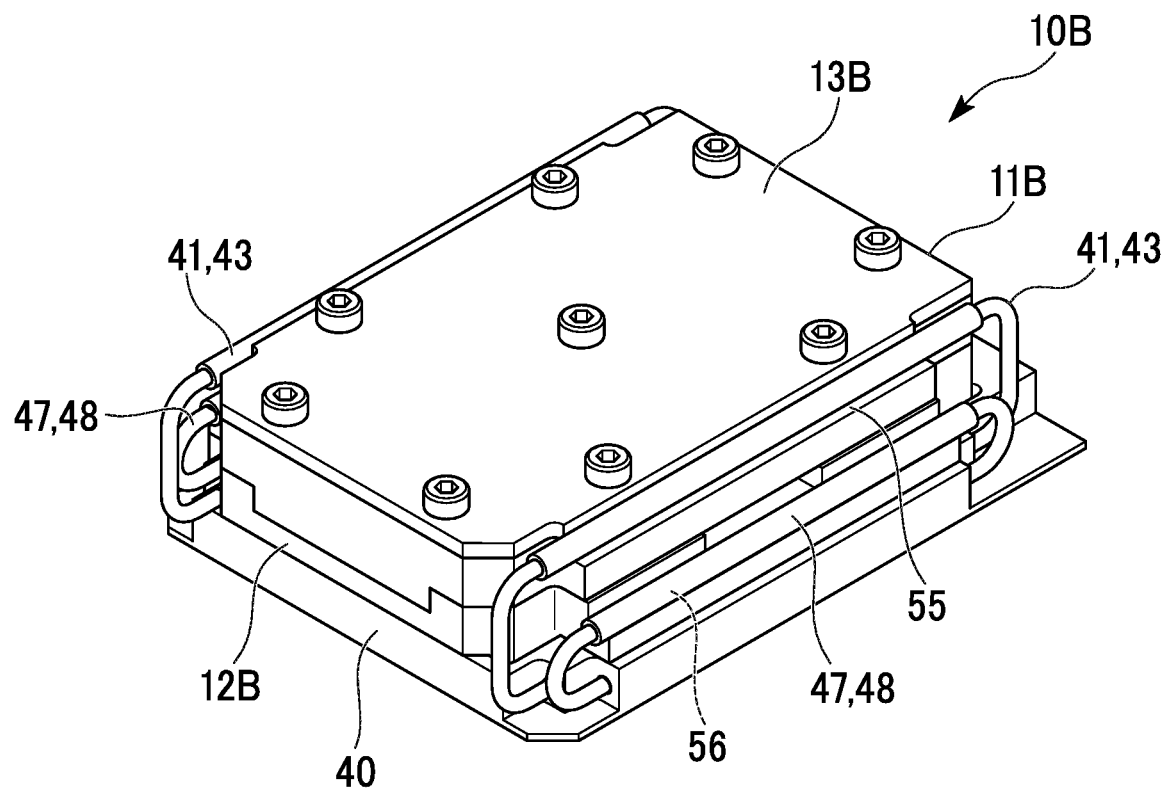
FIG. 6 is a perspective view showing a cell culture device of a third embodiment.
Figure 7:
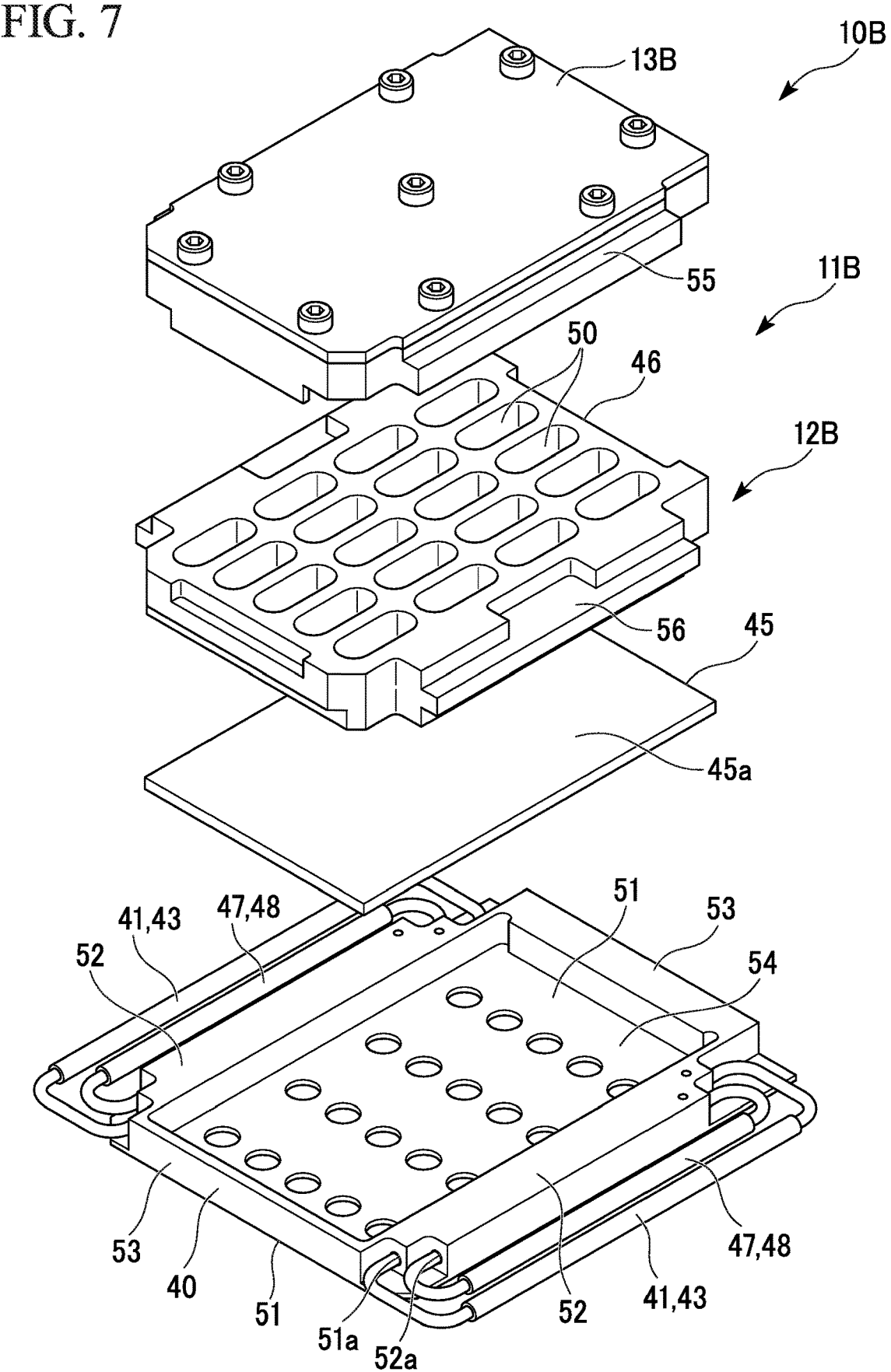
FIG. 7 is an exploded perspective view showing the cell culture device of FIG. 6.
Figure 8A:
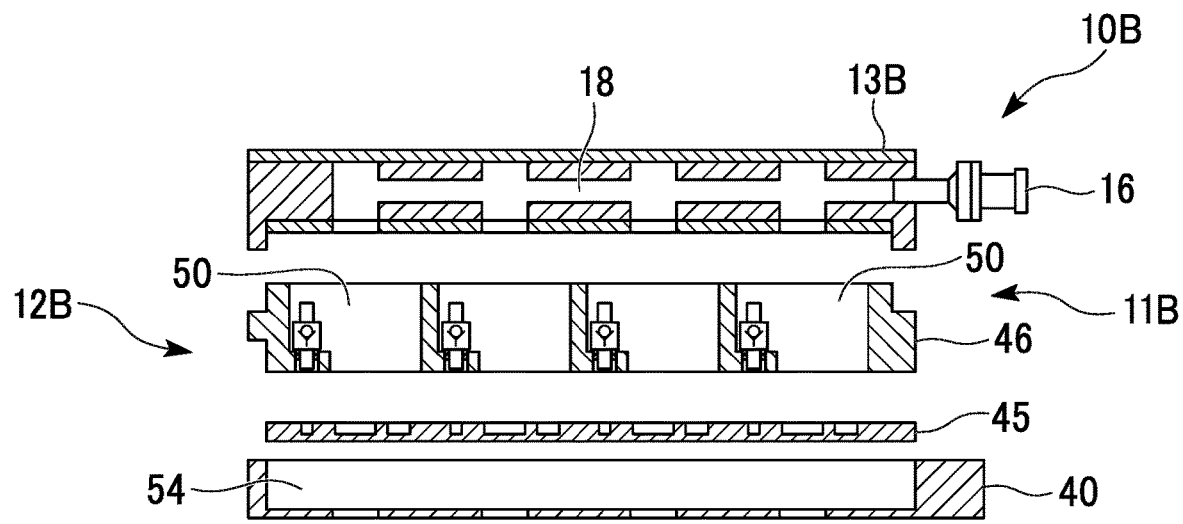
FIG. 8A is a front cross-sectional view of the cell culture device of FIG. 6 in a disassembled state.
Figure 8B:
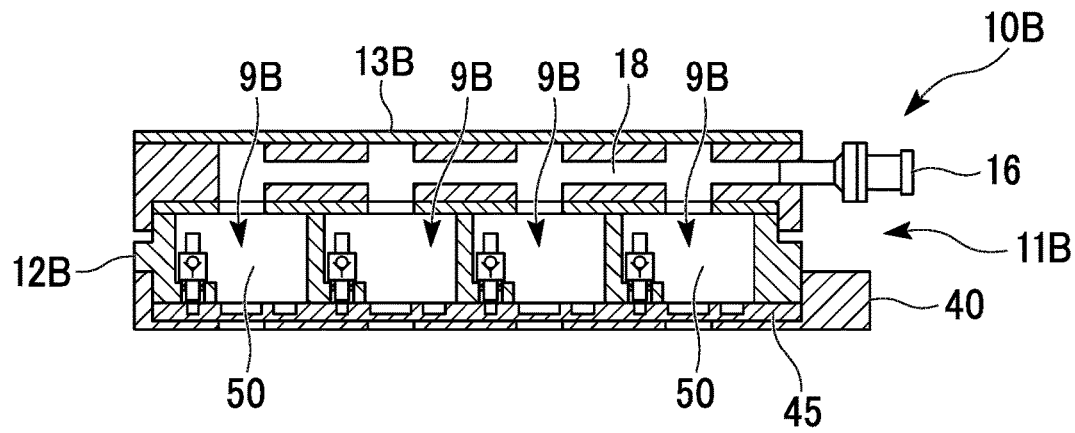
FIG. 8B is a front cross-sectional view of the cell culture device of FIG. 6.
Figure 9A:
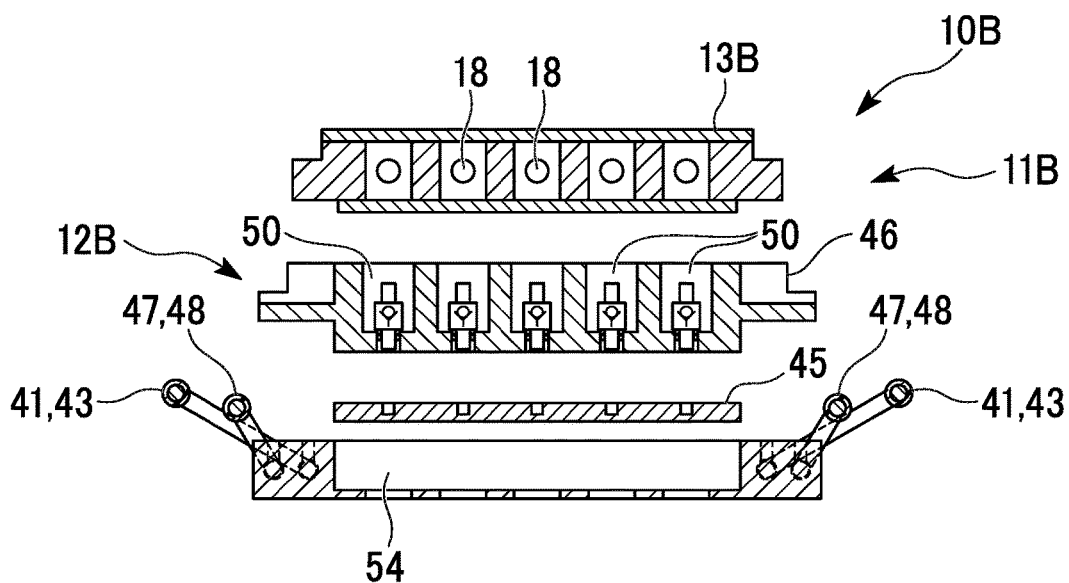
FIG. 9A is a side cross-sectional view of the cell culture device of FIG. 6 in a disassembled state.
Figure 9B:
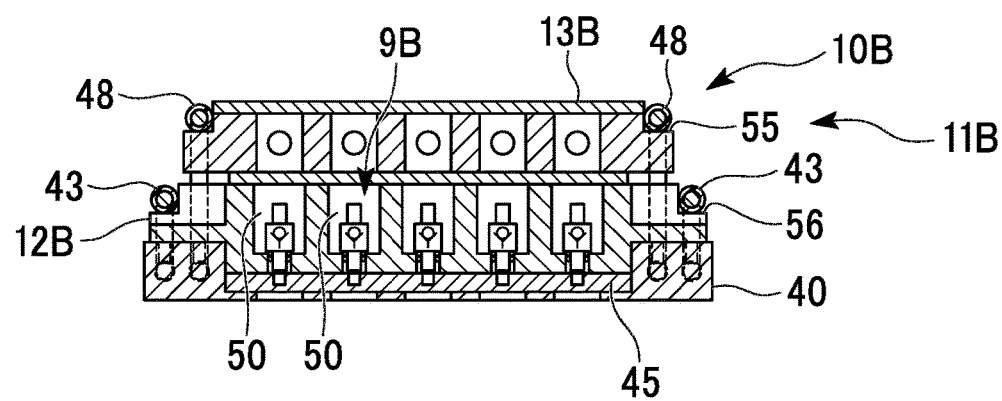
FIG. 9B is a side cross-sectional view of the cell culture device of FIG. 6.

FIG. 6 is a perspective view showing the cell culture device 10B. FIG. 7 is an exploded perspective view showing the cell culture device 10B. FIG. 8A is a front cross-sectional view of the cell culture device 10B in a disassembled state. FIG. 8B is a front cross-sectional view of the cell culture device 10B. FIG. 9A is a side cross-sectional view of the cell culture device 10B in a disassembled state. FIG. 9B is a side cross-sectional view of the cell culture device 10B.

As shown in FIGS. 6 to 9B, a storage tank 11B of the cell culture device 10B includes a plurality of cell culture units 9B (refer to FIG. 4).

The storage tank 11B includes a tank main body 12B, a lid portion 13B, a base body portion 40, a lid portion-pressing portion 41, and a wall portion-pressing portion 47.

The base body portion 40 includes a base plate 51, thick portions 52 and 52 formed so as to protrude upward from side edges of the base plate 51, and end wall portions 53 and 53 formed so as to protrude upward from end edges of the base plate 51. The base plate 51, the thick portions 52 and 52, and the end wall portions 53 and 53 define an accommodation space 54 for accommodating a bottom plate 45. An insertion hole 52a into which an end portion of a pressing bar 43 is inserted and an insertion hole 52b into which an end portion of a pressing bar 48 is inserted are formed on both end surfaces of the thick portion 52. The base body portion 40 supports the tank main body 12C placed on the base plate 51.

The lid portion-pressing portion 41 has a pair of pressing bars 43 (pressing members) for pressing the lid portion 13 toward the tank main body 12B. The pressing bar 43 is capable of moving rotationally around a central axis along the thick portion 52 in an axial direction in a state in which the both end portions are inserted into the insertion holes 52a, using the insertion portions as supporting points. The pressing bars 43 are capable of being engaged with engaging recess portions 55 formed on both side portions of the upper surface of the lid portion 13B. Accordingly, it is possible to hold the lid portion 13B in a state where the lid portion is pressed against the tank main body 12B and seal the internal space of the tank main body 12B.

The tank main body 12B includes a bottom plate 45 and a block-shaped wall portion 46 provided on an upper surface 45a (one surface) of the bottom plate 45.

The wall portion 46 has a plurality of through-hole portions 50 penetratingly formed in a thickness direction. The first culture liquid storage chamber 1, the second culture liquid storage chamber 2, the culture liquid main chamber 3, the first liquid storage chamber 21, and the second liquid storage chamber 22 are spaces partitioned by the through-hole portions 50 and the bottom plate 45. Each of the shapes in the plan views of the chambers 1, 2, 3, 21, 22 is oval.

A culture liquid introduction flow path 5, a culture liquid lead-out flow path 6, a communication flow path 7, a liquid introduction flow path 25, a liquid lead-out flow path 26, and a communication flow path 27 are formed in the bottom plate 45 (refer to FIG. 4).

The wall portion-pressing portion 47 has the pressing bar 48 (pressing member) for pressing the wall portion 46 toward the bottom plate 45. The pressing bar 48 is formed of, for example, metal, and is capable of moving rotationally around a central axis along the thick portion 52 in an axial direction in a state in which the both end portions are inserted into the insertion holes 52b, using the insertion portions as supporting points. The pressing bars 48 are capable of being engaged with engaging recess portions 56 formed on both side portions of the wall portion 46. Accordingly, it is possible to closely attach the wall portion 46 to the bottom plate 45 without any gap by pressing the wall portion to the bottom plate 45. The wall portion-pressing portion 47 is capable of holding the wall portion 46 in a state in which the wall portion is pressed against the bottom plate 45 using the pressing bar 48.

As shown in FIGS. 8A and 8B, it is preferable that at least two of the first culture liquid storage chambers 1 of the plurality of cell culture units 9B in the cell culture device 10B be connected with each other using a gas flow path 18. In addition, it is preferable that at least two of the second culture liquid storage chambers 2 of the plurality of cell culture units 9B be connected with each other using a gas flow path (not shown in the drawings). In addition, it is preferable that at least two of the first liquid storage chambers 21 of the plurality of cell culture units 9B be connected with each other using a gas flow path (not shown in the drawings). In addition, it is preferable that at least two of the second liquid storage chambers 22 of the plurality of cell culture units 9B be connected with each other using a gas flow path (not shown in the drawings).

In the cell culture device 10B, since the plurality of cell culture units 9B are connected with each other using the gas flow path 18 formed in the lid portion 13B, it is possible to collectively pressurize the storage chambers of the plurality of cell culture units 9B. For example, it is possible to collectively pressurize a plurality of first culture liquid storage chambers 1. Similarly, it is also possible to collectively pressurize the second culture liquid storage chamber 2, the first liquid storage chamber 21, and the second liquid storage chamber 22. For this reason, in the cell culture device 10B, it is possible to perform tests of the plurality of cell culture units 9B in parallel through a simple operation.

It is possible to use, for example, resin (plastic) or glass for the tank main body 12B and the lid portion 13B. Since it is easy to observe cells optically, it is preferable that the material be a transparent material and specifically preferably resin and glass.

Examples of resin include silicone resin (for example, polydimethylsiloxane (PDMS)), acrylic resin (for example, polymethyl methacrylate (PMMA)), styrene resin (for example, polystyrene), polyvinyl pyridine resin (such as poly(4-vinyl pyridine) or a 4-vinyl pyridine-styrene copolymer), polyolefin resin (for example, polyethylene resin, polypropylene resin, and polymethyl pentene resin), polyester resin (polyethylene terephthalate resin (PET)), polycarbonate resin, and epoxy resin.

Among these, silicone resin (for example, polydimethylsiloxane (PDMS)), acrylic resin (for example, polymethyl methacrylate (PMMA)), and styrene resin (for example, polystyrene) are preferable since they have high transparency.

Since the cell culture device 10B has the plurality of cell culture units 9B, it is possible to perform a plurality of tests in parallel. In addition, since the structure of the device can be simplified, it is possible to miniaturize the device by simplifying the structure of the device and to facilitate the operation such as setting of the device.

The cell culture device 10B is excellent in that it is possible to efficiently evaluate the influence a large number of specimens through a simple operation.

The configurations, the combinations thereof, and the like in the above-described embodiments are merely examples, and addition, omission, replacement, and other modifications of the configurations can be made within the scope not departing from the present invention. In addition, the present invention is not limited by each embodiment, but is limited only by the scope of the claims.

For example, although the storage tank 11B of the cell culture device 10B shown in FIG. 4 and the like has the tank main body 12B and the lid portion 13B, the present invention is not limited thereto, and an integral storage tank may be employed. The present embodiment is useful in the cell engineering field, the regenerative medical field, the bio-related industry field, the tissue engineering field, and the like. In particular, the present embodiment is useful for development of pharmaceutical products and basic research of cell biology.

DESCRIPTION OF REFERENCE NUMERAL 1 first culture liquid storage chamber
1d, 2d, 3d, 21d, 22d cell-holding recess portion (cell-holding portion)
1h, 2h, 21h, 22h vent hole
2 second culture liquid storage chamber
3 culture liquid main chamber
3a circulation space
4 membrane
4a inner surface (one surface)
5 culture liquid introduction flow path
6 culture liquid lead-out flow path
5a, 6a resistance flow path part
9, 9B, 9C cell culture unit
10, 10A, 10B, 10C cell culture device
11, 11A, 11B, 11C storage tank
12, 12B, 12C tank body
13, 13B, 13C lid portion
14 pressurizing pump (pressurizing means)
21 first liquid storage chamber
22 second liquid storage chamber
25 liquid introduction flow path
26 liquid lead-out flow path
32, 34, 36, 38 check valve
31, 35, 37 Laplace valve
41 lid portion-pressing portion
43 pressing bar (pressing member)
45 bottom plate
46 wall portion
47 wall portion-pressing portion
48 pressing bar (pressing member)
C1, C2 culture liquid
M1 liquid medium (liquid)

The invention claimed is:
1. A cell culture device, comprising:
a storage tank having one or a plurality of cell culture units and
a gas flow path, wherein each of the cell culture units comprises
- a culture liquid main chamber having a circulation space through which a culture liquid of cells circulates,
- a permeable membrane having one surface to which the cells are able to adhere, said one face facing the circulation space,
- a first culture liquid storage chamber having an airtight structure in which the culture liquid is to be stored,
- a second culture liquid storage chamber in which the culture liquid is to be stored,
- a culture liquid introduction flow path that introduces the culture liquid from the first culture liquid storage chamber into the circulation space of the culture liquid main chamber, and
- a culture liquid lead-out flow path that introduces the culture liquid from the circulation space into the second culture liquid storage chamber, and wherein the storage tank has a vent hole through which gas is supplied to and discharged from the first culture liquid storage chamber, and wherein the gas flow path is provided between at least two of the first culture liquid storage chambers in the plurality of the cell culture units connected with each other so that gas is able to flow therethrough, and the gas flow path is configured to collectively transfer the culture liquid among the plurality of the cell culture units using the gas flow path.

2. The cell culture device according to claim 1,
wherein each of the cell culture units includes
- a first liquid storage chamber having an airtight structure in which a liquid is to be stored,
- a second liquid storage chamber in which the liquid is to be stored, and
- a liquid lead-out flow path that introduces the liquid from a space on the other surface side of the membrane into the second liquid storage chamber, the first liquid storage chamber being a supply source of the liquid, and wherein the storage tank has a vent hole through which gas is supplied to and discharged from the first liquid storage chamber.

3. The cell culture device according to claim 2,
wherein at least two of the first liquid storage chambers in the plurality of the cell culture units are connected with each other so that gas is able to flow therethrough.

4. The cell culture device according to claim 1,
wherein the first culture liquid storage chamber and the second culture liquid storage chamber each have a cell-holding portion in which seeded cells are to be held.

5. The cell culture device according to claim 1, further comprising:
a backflow prevention mechanism that controls flow of the culture liquid from the culture liquid lead-out flow path to the second culture liquid storage chamber.

6. The cell culture device according to claim 5,
wherein the backflow prevention mechanism is a check valve which allows the flow of the culture liquid in a direction from the culture liquid lead-out flow path to the second culture liquid storage chamber and prevents flow in an opposite direction thereof.

7. The cell culture device according to claim 1, further comprising:
a backflow prevention mechanism that controls flow of the culture liquid from the first culture liquid storage chamber to the culture liquid introduction flow path.

8. The cell culture device according to claim 7,
wherein the backflow prevention mechanism is a Laplace valve which allows the flow of the culture liquid from the first culture liquid storage chamber to the culture liquid introduction flow path and prevents flow of gas from the first culture liquid storage chamber to the culture liquid introduction flow path.

9. The cell culture device according to claim 1,
wherein at least one of the culture liquid introduction flow path and the culture liquid lead-out flow path has a resistance flow path part of which a flow path cross-sectional area is less than or equal to $\frac{1}{10}$ of that of the other part.

10. The cell culture device according to claim 1,
wherein a distance of the circulation space in a thickness direction of the membrane is 1 μm to 1,000 μm.

11. The cell culture device according to claim 1,
wherein the storage tank has a container-shaped tank main body in which the culture liquid main chamber, the first culture liquid storage chamber, and the second culture liquid storage chamber are formed, and a lid portion that airtightly closes openings of the culture liquid main chamber, the first culture liquid storage chamber, and the second culture liquid storage chamber in an openable manner.

12. The cell culture device according to claim 11, further comprising:
a lid portion-pressing portion that holds the lid portion by pressing the lid portion toward the tank main body,
wherein the lid portion-pressing portion has a pressing member that presses the lid portion toward the tank main body.

13. The cell culture device according to claim 11,
wherein the tank main body includes a bottom plate having the liquid lead-out flow path, and a wall portion provided on one surface of the bottom plate, and
wherein the culture liquid main chamber, the first culture liquid storage chamber, and the second culture liquid storage chamber are spaces partitioned by the bottom plate and the wall portion.

14. The cell culture device according to claim 13, further comprising:
a wall portion-pressing portion that holds the wall portion by pressing the wall portion toward the bottom plate,
wherein the wall portion-pressing portion has a pressing member that presses the wall portion toward the bottom plate.

15. The cell culture device according to claim 1, further comprising:
pressurizing means capable of pressurizing an inside of the first culture liquid storage chamber.

16. A cell culture method, using the cell culture device according to claim 1, the method comprising:
supplying gas to the first culture liquid storage chamber through the vent hole to pressurize the first culture liquid storage chamber; and
introducing the culture liquid in the first culture liquid storage chamber into the culture liquid main chamber through the culture liquid introduction flow path with a pressure increase in the first culture liquid storage chamber, and introducing the culture liquid in the culture liquid main chamber into the second culture liquid storage chamber through the culture liquid lead-out flow path.

* * * * *